(12) United States Patent
Pei et al.

(10) Patent No.: US 6,894,048 B2
(45) Date of Patent: May 17, 2005

(54) SULFUR CONTAINING DIHYDROPHTHALAZINE ANTAGONISTS OF EXCITATORY AMINO ACID RECEPTORS

(75) Inventors: Xue-Feng Pei, Lansdale, PA (US); Baoqing Li, Collegeville, PA (US); Maria-Luisa Maccecchini, West Chester, PA (US)

(73) Assignee: Transgenomic, Inc., Omaha, NE (US)

( * ) Notice: Subject to any disclaimer, the term of this patent is extended or adjusted under 35 U.S.C. 154(b) by 0 days.

(21) Appl. No.: 10/667,069

(22) Filed: Sep. 18, 2003

(65) Prior Publication Data

US 2004/0058928 A1 Mar. 25, 2004

Related U.S. Application Data

(63) Continuation of application No. 09/833,855, filed on Apr. 12, 2001, now Pat. No. 6,703,390.
(60) Provisional application No. 60/196,823, filed on Apr. 13, 2000.

(51) Int. Cl.$^7$ ..................... A61K 31/502; C07D 237/30
(52) U.S. Cl. ....................... 514/248; 544/231; 544/234; 544/237
(58) Field of Search ................................. 544/231, 234, 544/237; 514/248

(56) References Cited

U.S. PATENT DOCUMENTS

| | | |
|---|---|---|
| 5,716,956 A | 2/1998 | Pelletier |
| 6,048,853 A | 4/2000 | Collins et al. |
| 6,329,370 B1 | 12/2001 | Napoletano et al. |

FOREIGN PATENT DOCUMENTS

| | | |
|---|---|---|
| DE | 196 17 863 | 10/1997 |
| WO | WO 96/40646 | 12/1996 |

OTHER PUBLICATIONS

Ikonomidou et al. Critical Reviews in Neurobiology, vol. 10(2), p. 239–263 (1996).*
Chen, et al., "Evaluation of five methods for testing anti-convulsant activities," *Proc. Soc. Exp. Biol. Med.* 87: 334–339 (1954).
Hussy, et al., "Functional properties of cloned 5–hydroxytryplamine ionotropic receptor subunit: comparison with native mouse receptors," *J. Physiol. (Lond.)* 481(2): 311–323 (1994).
Le Peillet, et al., "The non–NDMA antagonists, NBOX and GYKI 52466, protect against cortical and striatai cell loss following transient global ischaemia in the rat," *Brain Res.* 571: 115–120 (1992).
Lipton & Rosenberg, "Excitatory amino acids as a final common pathway for neurologic disorders," *N. Engl. J. Med.* 330: 613–622 (1994).
McBurney, "Therapeutic potential of NMDA antagonists in neurodegenerative diseases," *Neurobiol. Aging* 15: 271–273 (1994).
Meldrum, "Excitatory amino acids in epilepsy and potential novel therapies," *Epilepsy Res.* 12: 189–196 (1992).
*Remington's Pharmaceutical Sciences*, 17$^{th}$ ed., p. 1418 (1985).
Smith & Meldrum, "Cerebroprotective effect of a nonN–m-ethyl–O–aspartate antagonist, GYKI 52466, after focal ischemia in the rat," *Stroke* 23: 861–864 (!992).
Tarnawa, et al., "Electrophysiological studies with a 2,3–benzodiazepine muscle relaxant: GYKI 52466," *Eur. J. Pharmacol.* 167: 193–199 (1989).
Yamaguchi, et al., "Anticonvulsant activity of AMPA/kainate antagonists: comparison of GYK! 52466 and NBOX in maximal electroshock and chemoconvulsant seizure models," *Epilepsy Res.* 15: 179–184 (1993).

* cited by examiner

Primary Examiner—Richard L. Raymond
(74) Attorney, Agent, or Firm—Licata & Tyrrell P.C.

(57) ABSTRACT

Substituted dihydrophthalazine sulfur containing compositions are provided which are active as non-NMDA ionotropic excitatory amino acid (EAA) receptor antagonists. The compositions are useful for treating disorders associated with excessive activation of the non-NMDA subtype of the ionotropic EAA receptor. The compounds further are useful as testing agents to identify and characterize other compounds for the treatment of these disorders. The compounds are useful therapeutically as sedatives or for the treatment of neuropsychopharmacological disorders such as stroke, ischemia and epilepsy. The compositions may be provided in combination with a suitable carrier for oral or parenteral administration. The compounds may be administered orally or parenterally for the treatment of a variety of disorders associated with non-NMDA EEA receptor function.

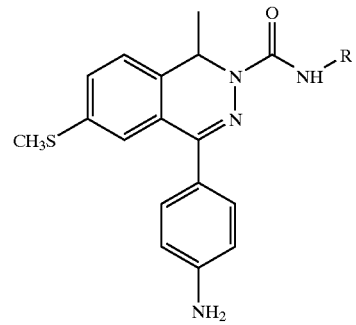

18 Claims, 1 Drawing Sheet

SYM 2257, R=*n*-Pr
SYM 2258, R=*n*-Bu
SYM 2259, R=Et

SYM 2260, R=*n*-Pr
SYM 2261, R=*n*-Bu
SYM 2262, R=Et

SERIES OF COMPOUNDS CONTAINING
6-METHYLTHIO GROUP

SULFUR CONTAINING DIHYDROPHTHALAZINE ANTAGONISTS OF EXCITATORY AMINO ACID RECEPTORS

CROSS-REFERENCE TO RELATED APPLICATIONS

This application is a continuation of U.S. patent application Ser. No. 09/833,855 filed Apr. 12, 2001 now U.S. Pat. No. 6,703,390 issued Mar. 9, 2004, which claims the benefit of U.S. Patent Application Ser. No. 60/196,823 filed Apr. 13, 2000.

BACKGROUND OF THE INVENTION

This invention relates to sulfur containing dihydrophthalazine compounds useful as antagonists of excitatory amino acid receptors.

During the past twenty-five years a great deal of attention has been directed toward the excitatory amino acids (EAA's), glutamate and aspartate, since they are believed to be the neurotransmitters responsible for the fast excitatory transmission in the mammalian central nervous system. The ionotropic EAA receptors are generally sub-classified into NMDA and non-NMDA receptors. These classifications are defined by those receptors which preferentially bind N-methyl-D-aspartate (NMDA) and those that are not responsive to NMDA but responsive to α-amino-3-hydroxy-5-methyl-4-isoxazoleproprionic acid (AMPA) or kainic acid (KA).

Tarnawa et al, describe 2,3-benzodiazepines (*Eur. J. Pharmacol.*, 167:193–199, 1989) which inhibit AMPA stimulated currents in neuronal cells. The 2,3-benzodiazepines such as GYKI 52466 and 53655 described by Tarnawa are noncompetitive AMPA antagonists which bind to a novel modulatory site on the AMPA receptor. Meldrum (*Stroke*, 23:861, 1992 & *Brain Res.*, 571:115, 1992) has shown that GYKI 52466 is effective in rat models of both global and focal ischemia. GYKI 52466 was effective in a middle cerebral artery occlusion (MCAO) model of ischemia when given either continuously for 2 hours just after occlusion or delayed for one hour. The compounds reduced cortical infarct volumes by 68% and 48% respectively. In another model of neurodegenerative disease, GYKI 52466 was as effective as the glutamate site competitive antagonist NBQX in rat common carotid arteries model of global ischemia. These two animal models suggest that these compounds may be useful for the treatment of stroke and neurodegenerative ischemic conditions.

Efforts to find NMDA receptor antagonists and blockers which are neuroprotective have been very successful while efforts to find specific non-NMDA receptor antagonists have been much less successful. A number of pharmaceutical companies have pursued development of ion channel blockers or full antagonists of the NMDA receptor to protect against both chronic and acute neurodegenerative processes. Although some compounds have entered clinical trials, there has been only limited progress in developing a clinically useful NMDA receptor antagonist. Some useful compounds, namely substituted dihydrophthialazines, have been described for use as non-NMDA receptor antagonists (U.S. Pat. No. 5,716,956). These compounds are particularly useful because they bind to KA and/or AMPA receptors directly.

It is an object of the invention to provide compounds which are useful as non-NMDA glutamate receptor antagonists as well as methods for their synthesis.

It is a further object of the invention to provide non-NMDA receptor antagonists which are useful as sedatives or for the treatment of neuropsychopharmacological disorders such as stroke, ischemia and epilepsy.

It is yet another object of the invention to provide compounds which are useful for the treatment of neurological, neuropsychiatric, neurogenerative and functional disorders associated with excessive activation of the non-NMDA subtypes of the ionotropic EAA receptor.

BRIEF SUMMARY OF THE INVENTION

Compositions are provided which are active as non-NMDA ionotropic excitatory amino acid (EAA) receptor antagonists, in particular, which bind to the KA and/or AMPA receptors, and which therefore are useful for treating disorders associated with excessive activation of the non-NMDA subtypes of the ionotropic EAA receptors. The compounds further are useful as testing agents to identify and characterize other compounds for the treatment of these disorders.

Illustrative compounds include:

4-(4-Aminophenyl)-1,2-dihydro-1-methyl-2-ethylcarbamoyl-6-methylthiophthalazine, 4-(4-Aminophenyl)-1,2-dihydro-1-methyl-2-n-propylcarbamoyl-6-methylthiophthalazine, 4-(4-Aminophenyl)-1,2-dihydro-1-methyl-2-n-butylcarbamoyl-6-methylthiophthalazine, 4-(4-Aminophenyl)-1,2-dihydro-2-ethylcarbamoyl-6-methylthiophthalazine, 4-(4-Aminophenyl)-1,2-dihydro-2-n-propylcarbamoyl-6-methylthiophthalazine, 4-(4-Aminophenyl)-1,2-dihydro-2-n-butylcarbamoyl-6-methylthiophthalazine.

The compositions may be provided in combination with a suitable carrier for oral or parenteral administration. The compounds may be administered orally or parenterally for the treatment of a variety of disorders associated with non-NMDA glutamate receptor function. The composition may be used, for example, as sedatives or for the treatment of neuropsychopharmacological disorders such as stroke, ischemia and epilepsy.

DETAILED DESCRIPTION OF THE INVENTION

Figure 1:
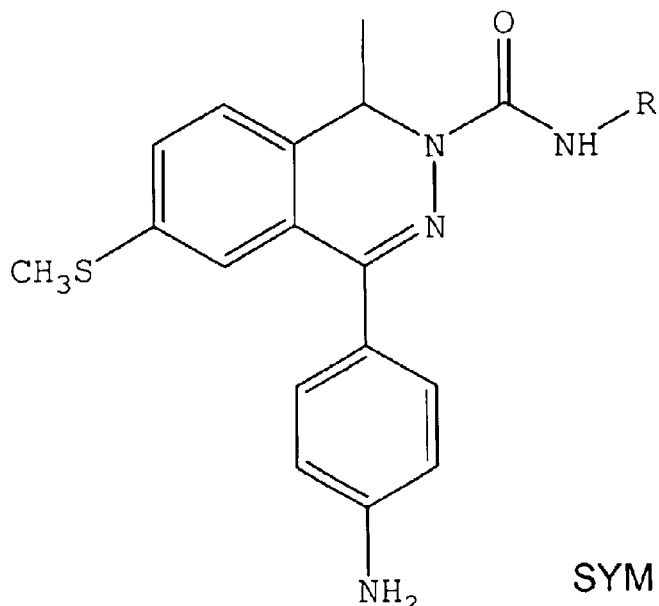
FIG. 1 is a diagram of the structures of SYM 2257(4-(4-Aminophenyl)-1,2-dihydro-1-methyl-2-n-propylcarbamoyl-6-methylthiophthalazine), SYM 2258(4-(4-Aminophenyl)-1,2-dihydro-1-methyl-2-n-butylcarbamoyl-6-methylthiophthalazine), SYM 2259(4-(4-Aminophenyl)-1,2-dihydro-1-methyl-2-ethylcarbamoyl-6-methylthiophthalazine), SYM 2260(4-(4-Aminophenyl)-1,2-dihydro-2-n-propylcarbamoyl-6-methylthiophthalazine), SYM 2261 (4-(4-Aminophenyl)-1,2-dihydro-2-n-butylcarbamoyl-6-methylthiophthalazine), and SYM 2262 (4-(4-Aminophenyl)-1,2-dihydro-2-ethylcarbamoyl-6-methylthiophthalazine).
Figure 1:
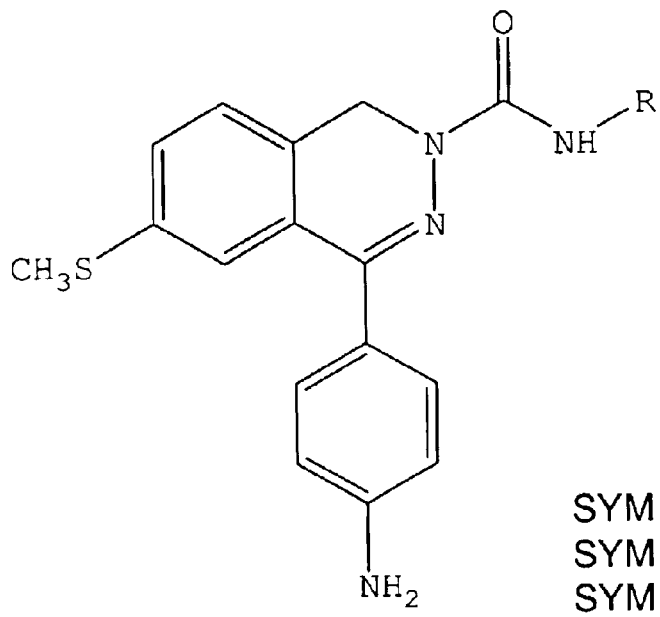

I. Glossary of Terms.

The term "antagonist" as used herein means any compound which reduces the flow of cations through the non-NMDA receptor.

The term "neuropsychopharmacological disorder" as used herein means a disorder resulting from or associated with an excessive flux of ions through the AMPA receptor ligand-gated cation channels, and includes chemical toxicity (including substance tolerance and addiction), excitotoxicity, neurodegenerative disorders (such as Huntington's disease, Parkinson's disease, and Alzheimer's disease), post-stroke sequelae, epilepsy, seizures, mood disorders (such as bipolar disorder, dysthymia, and seasonal affective disorder), and depression. Neurodegenerative disorders can result from dysfunction or malfunction of the AMPA receptor.

The term "NMDA receptor" as used herein means a receptor which is stimulated, at a minimum, by the excitatory amino acids glutamic acid as well as by NMDA, but is not stimulated by AMPA or KA. It is a ligand-gated receptor.

The term "AMPA receptor" as used herein means a receptor which is stimulated, at a minimum, by the excitatory amino acids glutamic acid as well as by AMPA, but is not stimulated by NMDA. It is a ligand-gated receptor.

The term "Kainate receptor" as used herein means a receptor which is stimulated, at a minimum, by the excitatory amino acids glutamic acid as well as by KA, but is not stimulated by NMDA or AMPA. It is a ligand-gated receptor.

Pharmaceutically acceptable salts include both the metallic (inorganic) salts and organic salts; a list of which is given in Remington's Pharmaceutical Sciences 17th Edition, p. 1418 (1985). It is well known to one skilled in the art that an appropriate salt form is chosen based on physical and chemical stability, flowability, hygroscopicity and solubility.

Throughout this application when an alkyl substituent is identified, the normal alkyl structure is intended (i.e. butyl is n-butyl) unless otherwise specified. However, when radicals are identified (e.g. $R^5$), both branched and straight chains are included in the definition of alkyl, alkenyl, and alkynyl.

II. Compositions With Non-NMDA Receptor Antagonist Properties.

A. Compounds of Formula I

Compounds of Formula I are provided which are active as non-NMDA ionotropic EAA receptor antagonists.

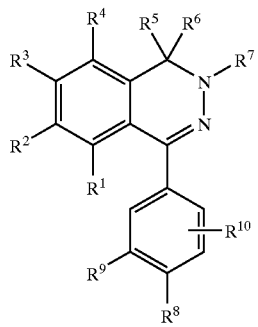

where $R^1$, $R^2$, $R^3$ and $R^4$ are independently

H,

HO, $R^{11}O—$ halogen (F, Cl, Br), $C_1$–$C_3$-alkyl, $CF_3$, $R^{12}CO_2—$, $R^{12}O_2C—$, $R^{12}CO—$, $R^{12}CONH—$, $R^{12}NHCO—$, $R^{12}NHCO_2—$, $R^{12}OCONH—$, $R^{12}O_2S—$, $R^{12}OS—$, or $R^{13}R^{14}N—$; or $R^1$ and $R^2$, or $R^2$ and $R^3$, or $R^3$ and $R^4$ taken together can be

—SCH$_2$S—,

—SCH$_2$O—,

—OCH$_2$S—,

—SCH$_2$CH$_2$S—,

—SCH$_2$CH$_2$O—, or

—OCH$_2$CH$_2$S—;

wherein at least one of $R^1$, $R^2$, $R^3$ and $R^4$ must be a $C_1$–$C_3$-alkylthio group, $R^5$ and $R^6$ are independently

H, $C_1$–$C_6$-alkyl, $C_3$–$C_6$-alkenyl, $C_3$–$C_6$-cycloalkyl, or phenyl or substituted phenyl, where the phenyl is substituted with one or two substituents selected from the group consisting of C1–C3-alkyl, halogen (F, Cl, Br), $R^{11}O—$, $CF_3—$, $R^{12}O_2S—$, $R^{12}OS—$, $R^{12}CO$, $R^{12}CO_2—$, $R^{12}O_2C—$, $R^{12}CONH—$, $R^{12}NHCO—$, $R^{12}—NHCO_2—$, $R^{12}OCONH$, and $R^{13}R^{14}N—$; or $R^5$ and $R^6$ taken together can be C3–C6-cycloalkyl;

$R^7$ is $R^{13}R^{14}NCO—$, $R^{13}R^{14}NCS—$, $R^{13}R^{14}N(CR^{15})—$, $R^{15}OCO—$, $R^{13}CO—$, $R^{13}R^{14}NCH_2CO—$, $R^{12}O_2C—(CH_2)_n—$, $R^{13}R^{14}NCO—(CH_2)_n—$, $NC—(CH_2)_n—$,

H,

C1–C6-alkyl,

C3–C6-alkenyl, or

C3–C6-cycloalkyl; or $R^6$ and $R^7$ taken together can be

—(CH$_2$)$_m$CH$_2$(R$^{13}$)NCO—,

—(CH$_2$)$_m$CH$_2$OCO—, or

—(CH$_2$)$_m$CH$_2$CH$_2$CO—;

$R^8$ and $R^9$ are independently

H, $R^{13}R^{14}N—$, $R^{13}R^{14}N(CR^{15})—$, $R^{12}HNCO—$, or $R^{12}CONH—$;

$R^{10}$ is

H, halogen (F, Cl, Br),

HO, $R^{11}O—$, $R^{13}R^{14}N—$,

C1–C3-alkyl, $CF_3$, $R^{12}CO_2—$,

R$^{12}$CO—, or
R$^{12}$CONH—;
R$^{11}$ is C1–C3-alkyl;
R$^{12}$ is H or C1–C3-alkyl;
R$^{13}$ and R$^{14}$ are independently
H,
C1–C10-alkyl,
C1–C6-perfluoroalkyl,
C3–C10-alkenyl, or
C3–C6-cycloalkyl; or
R$^{13}$ and R$^{14}$ taken together can be C3–C6-cycloalkyl;
R$^{15}$ is C1–C6-alkyl, C3–C6-alkenyl, or C3–C6-cycloalkyl;
n is 1 to 6;
m is 0 to 2;
and pharmaceutically acceptable salts thereof;
where R$^8$ and R$^9$ cannot be both be H.
Preferred compounds are compounds of Formula I where:
one of four substituents of R$^1$, R$^2$, R$^3$ and R$^4$ must be C1–C3-alkylthio group, the other substituents are independently H, R$^{11}$O—, R$^{11}$S—, halogen (F, Cl, Br), or C1–C3-alkyl;
R$^2$ and R$^3$ taken together can be —SCH$_2$S—, —SCH$_2$O—, or —OCH$_2$S—;
R$^7$ is
R$^{13}$R$^{14}$NCO—,
R$^{13}$R$^{14}$NCS—,
R$^{13}$R$^{14}$N(CR$^{15}$)—,
R$^{15}$OCO—,
R$^{13}$CO—, or
H;
R$^8$ and R$^9$ are independently H, H$_2$N— or CH$_3$CONH—;
and pharmaceutically acceptable salts thereof.
Specifically preferred are:
4-(4-Aminophenyl)-1,2-dihydro-1-methyl-2-ethylcarbamoyl-6-methylthiophthalazine (SYM 2259),
4-(4-Aminophenyl)-1,2-dihydro-1-methyl-2-n-propylcarbamoyl-6-methylthiophthalazine (SYM 2257),
4-(4-Aminophenyl)-1,2-dihydro-1-methyl-2-n-butylcarbamoyl-6-methylthiophthalazine (SYM 2258),
4-(4-Aminophenyl)-1,2-dihydro-2-ethylcarbamoyl-6-methylthiophthalazine (SYM 2262),
4-(4-Aminophenyl)-1,2-dihydro-2-n-propylcarbamoyl-6-methylthiophthalazine (SYM 2260), and
4-(4-Aminophenyl)-1,2-dihydro-2-n-butylcarbamoyl-6-methylthiophthalazine (SYM 2261).

B. Compounds of Formula II

Compounds of Formula II are provided which are active as non-NMDA ionotropic EAA receptor antagonists.

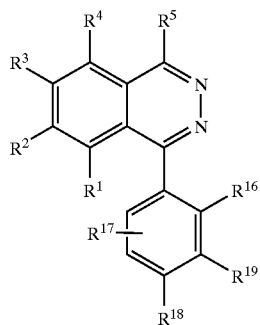

where
R$^1$, R$^2$, R$^3$ and R$^4$ are independently
H,
HO,
R$^{11}$O—,
halogen (F, Cl, Br),
C1–C3-alkyl,
CF$_3$,
R$^{12}$CO$_2$—,
R$^{12}$O$_2$C—,
R$^{12}$CO—,
R$^{12}$CONH—,
R$^{12}$NHCO—,
R$^{12}$NHCO$_2$—,
R$^{12}$OCONH—,
R$_{12}$O$_2$S—,
R$^{12}$OS—, or
R$^{13}$R$^{14}$N—; or
R$^1$ and R$^2$, or R$^2$ and R$^3$, or R$^3$ and R$^4$ taken together can be
—SCH$_2$S—,
—SCH$_2$O—
—OCH$_2$S—
—SCH$_2$CH$_2$S—,
—SCH$_2$CH$_2$O—, or
—OCH$_2$CH$_2$S—;
wherein at least one of R$^1$, R$^2$, R$^3$ and R$^4$ must be a C1–C3-alkylthio group;
R$^5$ is
H,
C1–C6-alkyl,
C3–C6-alkenyl,
C3–C6-cycloalkyl,
phenyl or substituted phenyl, where the phenyl is substituted with one or two substituents selected from the group consisting of C1–C3-alkyl, halogen (F, Cl, Br), R$^{11}$O—, CF$_3$—, R$^{12}$O$_2$S—, R$^{12}$OS—, R$^{12}$CO, R$^{12}$CO$_2$—, R$^{12}$O$_2$C—, R$^{12}$CONH—, R$^{12}$NHCO—, R$^{12}$NHCO$_2$—, R$^{12}$OCONH, or R$^{13}$R$^{14}$N—;
R$^{11}$ is C1–C3-alkyl;
R$^{12}$ is H or C1–C3-alkyl;
R$^{13}$ and R$^{14}$ are independently
H,
C1–C10-alkyl,
C1–C6-perfluoroalkyl,
C3–C10-alkenyl, or
C3–C6-cycloalkyl; or
R$^{13}$ and R$^{14}$ taken together can be C3–C6-cycloalkyl;
R$^{15}$ is C1–C6-alkyl, C3–C6-alkenyl, or C3–C6-cycloalkyl;
R$^{16}$ and R$^{17}$ are independently
H,
halogen (F, Cl, Br),
C1–C3-alkyl,
R$^{12}$O—,
CF$_3$—, or
R$^{12}$CO$_2$—;
R$^{18}$ and R$^{19}$ are independently
H,
R$^{13}$R$^{14}$N—,
R$^{13}$HNC(NH)—, or
R$^{12}$CONH—;

and pharmaceutically acceptable salts thereof;
where $R^{18}$ and $R^{19}$ cannot both be H.

Preferred compounds are compounds of Formula II where:
one of four substituents of $R^1$, $R^2$, $R^3$ and $R^4$ must be a C1–C3-alkylthio group, the other substituents are independently H, $R^{11}O$—, $R^{11}S$—, halogen (F, Cl, Br), or C1–C3-alkyl;
$R^2$ and $R^3$ taken together can be —$SCH_2S$—, —$SCH_2O$—, or —$OCH_2S$—;
$R^{18}$ and $R^{19}$ are independently H, $H_2N$—, or $CH_3CONH$';
and pharmaceutically acceptable salts thereof.

Specifically preferred are:
1-(4-Aminophenyl)-6-methylthiophthalazine,
1-(4-Acetylaminophenyl)-6-methylthiophthalazine,
1-(4-Aminophenyl)-7-methylthiophthalazine,
1-(4-Acetylaminophenyl)-7-methylthiophthalazine,
1-(4-Aminophenyl)-4-methyl-6-methylthiophthalazine,
1-(4-Acetylaminophenyl)-4-methyl-6-methylthiophthalazine,
1-(4-Aminophenyl)-4-methyl-7-methylthiophthalazine,
1-(4-Acetylaminophenyl)-4-methyl-7-methylthiophthalazine.

The compounds of Formulas I and II may be combined with a suitable pharmaceutical carrier and used to treat neurological, neuropsychological, neuropsychiatric, neurodegenerative, neuropsychopharmacological and functional disorders associated with excessive activation of the non-NMDA subtype of the ionotropic EAA receptors. The compounds can also be used as testing agents to identify and characterize other compounds for the treatment of acute and chronic neurodegenerative diseases, seizures, depression, anxiety and substance addiction.

III. Synthesis

The compounds of Formulas I and II may be prepared using synthetic reactions and techniques available in the art, as described, for example in March, "Advanced Organic Chemistry," 4th Edition, 1992, Wiley-Interscience Publication, New York. The reactions are performed in solvents suitable to the reagents and materials employed and suitable for the transformation being effected. Depending upon the synthetic route selected, and the functionality of the starting material or intermediates, the appropriate protection groups and deprotection conditions available in the art of organic synthesis may be utilized in the synthesis of the compound.

In one embodiment, compounds of Formulas I and II may be synthesized as outlined in Scheme 1.

Scheme 1

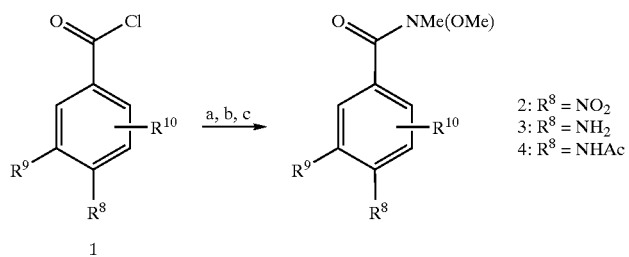

2: $R^8 = NO_2$
3: $R^8 = NH_2$
4: $R^8 = NHAc$

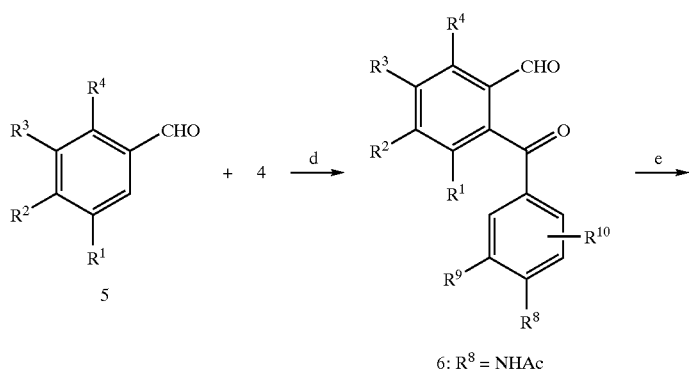

6: $R^8 = NHAc$

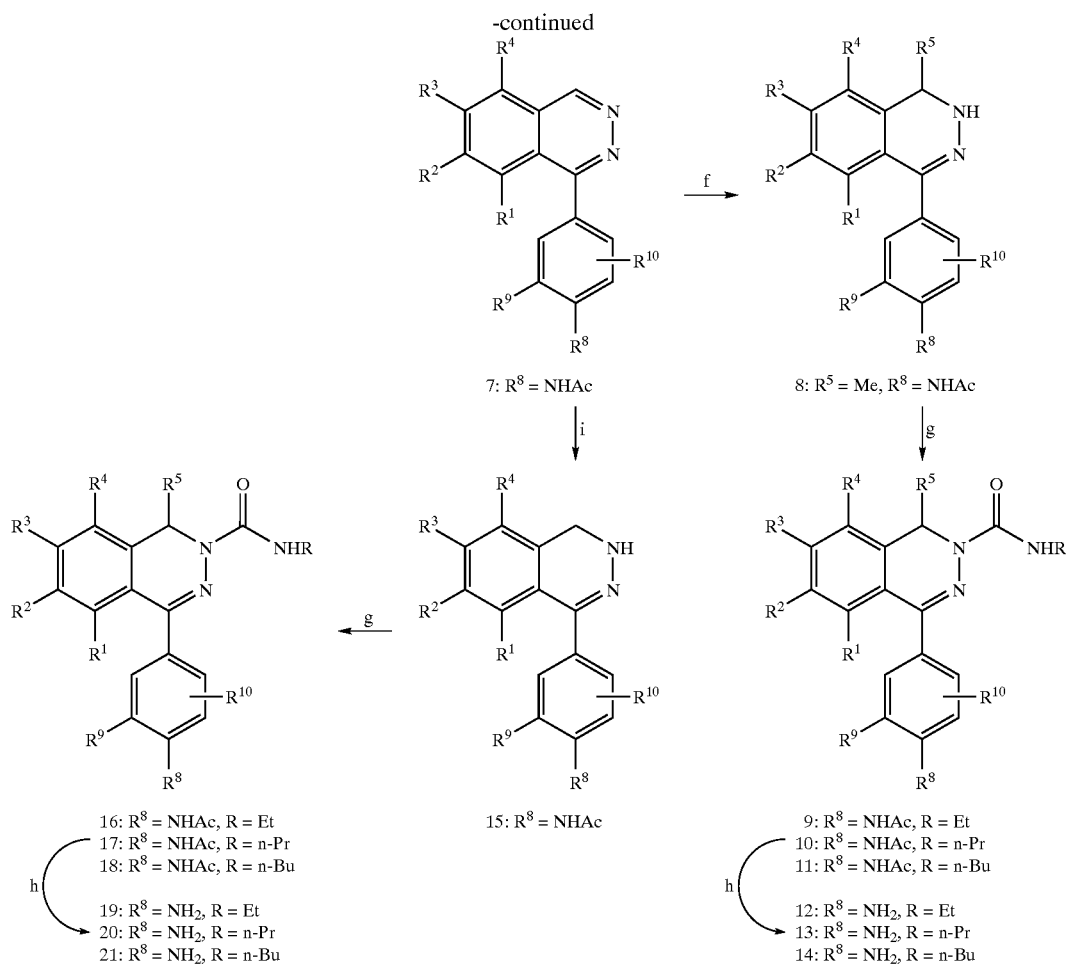

Reaction conditions: (a) HNMe(OMe)HCl, Py, DCM (70%); (b) H₂, Pd/C, MeOH; (c) Ac₂O, DMAP, DCM; (d) n-BuLi, TMEDA, THF, -20° C.; (e) H₂NNH₂H₂O, EtOH, reflux; (f) MeLi, THF, 0° C.; (g) RCNO, DCM, rt; (h) 2N NaOH, MeOH, reflux; (i) NaBH₃CN, CH₃COOH.

Protected amides 4 can be prepared from appropriate acids or acid chlorides by treatment of the acid chloride or acid anhydride with N,O-dimethylhydroxylamine in an inert solvent such as methylene chloride or tetrahydrofuran and a base such as pyridine at a temperature of −10° to 0° C. for 1–8 hours to yield amides 2 which can be converted to anilines 3 by reducing the nitro group by hydrogenation over a catalyst such as 10% Pd/C or 5% Pd/C in a solvent such as methanol at a pressure from atmospheric pressure to 60 psi for 30 minutes to 6 hours. The anilines 3 can be protected as amides by treatment with acetyl chloride or acetic anhydride in an inert solvent such as methylene chloride and a base such as 4-dimethylaminopyridine.

The substituted benzophenones 6 are prepared by reacting the lithiated derivative of aldehydes 5, which is generated by reacting 5 with a reagent such as n-butyl lithium and N,N,N'-trimethylethylenediamine in an inert solvent such as tetrahydrofuran at a temperature of −110 to −20° C. for 10 minutes to 24 hours, with amides 4 at a temperature of −78 to 25° C. for 2–24 hours. The benzophenones 6 are then converted to phthalazines 7 by treatment with hydrazine in a solvent such as ethanol at a temperature 0° C. to reflux of the solvent for 6–24 hours.

The 1-alkyl-dihydrophthalazines 8 are prepared by reacting phthalazines 7 with an alkyl lithium or Grignard reagent in an inert solvent such as tetrahydrofuran at a temperature of −78 to 25° C. for 1–6 hours. Tile dihydrophthalazines 8 can then be treated with an acylating reagent such as acid chloride, an alkylisocyanate, an alkylisothiocyanate, an alkylchloroformate or chloroamidate in an inert solvent such as methylene chloride with a base such as dimethylamino pyridine (DMAP) at a temperature 0° C. to reflux of the solvent for 6–48 hours. The acetanilide protecting can then be removed by careful treatment with a base such as NaOH in a solvent such as methanol at a temperature 25° C. to reflux of the solvent for 2–72 hours.

The 1-unsubstituted dihydrophthalazines 14 are prepared by reacting phthalazines 7 with a reducing reagent such as NaBH₃CN in a solvent such as acetic acid at temperature of 0 to 25° C. for 15 minutes to 6 hours. The dihydrophthalazines 14 can then be treated with an acylating reagent such as acid chloride, an alkylisocyanate, an alkylisothiocyanate, an alkylchloroformate or chloroamidate in an inert solvent such as methylene chloride with a base such as dimethylamino pyridine (DMAP) at a temperature 0° C. to reflux of the solvent for 6–48 hours. The acetanilide protecting can then be removed by careful treatment with a base such as NaOH in a solvent such as methanol at a temperature 25° C. to reflux of the solvent for 2–72 hours.

IV. In Vitro and In Vivo Assays of Activity and Therapeutic Efficacy

In vivo and in vitro assays may be conducted to determine the activity of the compounds as antagonists of the non- NMDA receptors, i.e., the ionotropic EAA receptors which bind AMPA or KA. In combination, in vitro and in vivo assays are predictive of the activity of these compounds for treatment of patients. This is supported, for example, by numerous studies in the literature illustrating that in vitro and hi vivo studies of NMDA receptor modulation by a test compound provide a good indication of the compound's efficacy in treating disorders associated with excessive activation of the NMDA receptor. See, for example: Meldrum *Epilepsy Research,* 12:189–196 (1992); Lipton and Rosenberg, *New England Journal of Medicine,* 330:613–622 (1994); and McBurney, *Neurobiology of Aging,* 15:271–273 (1994).

A. Electrophysiology

The potency of the disclosed compounds for drug inhibition of the AMPA receptor can be tested using the whole-cell patch clamp technique on primary cultures of rat neocortex. The general procedure for stimulating AMPA-receptor mediated currents with KA and for the measurement of current inhibition is based on that used by Donevan and Rogawski (*Neuron,* 10: 51–59, 1993) for 2,3-benzodiazepines.

Standard extracellular bath solutions and intracellular pipette solutions are used as described in detail by Hussy and coworkers (*J. Physiol.* (Lond.), 481.2: 311–323, 1994). The drug application system is designed to allow rapid switching between 7 different reservoirs containing either control bath solution, kainic acid (50 $\mu$M), or kainic acid (50 $\mu$M) plus antagonist (10 $\mu$M). Each recording is begun with a control response to KA alone.

Following the establishment of a 2–3 sec duration steady baseline, bathing solution is switched to one containing KA plus antagonist for an additional 2–3 sec period. Alternatively, 5 different doses of a single compound are tested for the determination of the antagonist $IC_{50}$.

B. Neurodegenerative Transient Global Forebrain Ischemia

The extent of protection by a test compound in a model of brain ischemia may be assayed as described by Meldrum et al. (*Brain Res.,* 571:115, 1992), and references cited therein. Male Wistar rats (250–300 g) are anesthetized using halothane-oxygen-nitrogen mixture and both vertebral arteries are permanently occluded by electrocauterisation within the alar foraminae of the first cervical vertebra. At the same time, both common carotid arteries are isolated and atraumatic clamps placed around each one. One femoral vein is cannulated to enable the subsequent iv administration of fluid. The following day cerebral ischemia is induced in the unanaesthetised animal, by tightening the clamps around the carotid arteries for 20 min. Carotid clamping results. Body temperature is maintained at 37° C. by use of a rectal probe and hot plate. Seven days after the ischemic insult rats are sacrificed and the brains processed for light microscopy. Neuroprotection is assessed by examination of the extent of damage in the cortex and hippocampus. Compounds may be selected which are active in this model.

C. Neurodegenerative Permanent Focal Ischemia

The extent of protection by a test compound in a model of brain ischemia may be tested using a model described by Meldrum and Smith (*Stroke,* 23:861, 1992), and references cited therein. Male Fisher F344 rats (210–310 g) are anesthetized with halothane-oxygen-nitrogen mixture receive a small incision between the eye and ear, the mandibular muscles are retracted to expose the orbit and zygomatic arch. A small craniotomy is made to expose the base of the middle cerebral artery. Bipolar coagulation is used to permanently occlude the artery at the base. One day after the ischemic insult rats are sacrificed and the brains processed for light microscopic examination. Lesion volume is determined by using Cavalarei's principle. Compounds may be selected which are active in this model.

D. Maximum Electro Shock (MES) Seizure Test

The extent of protection by a test compound in a seizure model is tested as described by Rogawski et al. (*Epilepsy Research,* 15:179–184, 1993). Male NIH Swiss mice (25–30 g) are injected ip with the test drug. The mice are subjected to a 0.2 sec, 60 Hz, 50 mA electrical stimulus delivered with corneal electrodes wetted with 0.9% saline at 15–30 min post dosing. Animals failing to show tonic hind limb extension are scored as protected. Compounds may be selected which are active in this model.

E. Subcutaneous Metrazol (scMET) Seizure Test

This test can be used to determine the extent of protection by a test compound in a seizure model. The method used is that of Chen et al. (*Proc. Soc. Exp. Biol. Med.,* 87:334, 1954). Mice are randomly assigned to vehicle or treatment groups of 3–10 animals per group and then dosed accordingly. Metrazol (pentylenetetrazol) 90 mg/kg is administered subcutaneously (sc) at different time points (0.25, 0.5, 1, 2, 4 hr) after the treatment or control groups. The mice individually housed in clear runs and observed for the presence or absence of clonic seizure activity (>5 s duration) for 30 min after metrazol dosing. A compound is considered active if no seizure is observed. Data is analyzed using a quantal measure (protection/number tested).

V. Dosage Forms

The disclosed compounds can be administered parenterally, that is, subcutaneously, intramuscularly, or intravenously and, alternatively administered orally, in a dose range of between about 0.01 and 100 mg/kg body weight.

The active ingredient can be administered parenterally in sterile liquid dosage forms. In general, water, a suitable oil, saline, aqueous dextrose, and related sugar solutions and glycols such as propylene glycol or polyethylene glycols are suitable carriers for parenteral solutions. Solutions for parenteral administration preferably contain a water soluble form of the active ingredient, suitable stabilizing agents, and, if necessary, buffer substances. Antioxidizing agents such as sodium bisulfite, sodium sulfite, or ascorbic acid either alone or combined are suitable stabilizing agents. Also used are citric acid and its salts and sodium EDTA. In addition, parenteral solutions can contain preservatives, such as benzalkonium chloride, methyl- or propylparaben, and chlorobutanol.

The active ingredient can be administered orally in solid dosage forms, such as capsules, tablets and powders, or in liquid dosage forms, such as elixirs, syrups, and suspensions. Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. The active ingredients also may be provided in a particle for sustained or pulsed delivery such as a liposome or microcapsule. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance. Suitable pharmaceutical carriers are described in Remington's Pharmaceutical Sciences, a standard reference text in this field.

Optionally, the compounds either alone or in combination with a carrier may be administered by implantation or by application to a mucosal surface, for example, the nasal-pharyngeal region and/or lungs using all aerosol or may be administered to a skin surface via a topical carrier such as a cream or lotion.

The compounds of this invention and their preparation can be understood further by the following non-limiting examples which describe the synthesis of exemplary compounds. In these examples, unless otherwise indicated, all temperatures are in degrees Celsius and parts and percentages are by weight.

EXAMPLES

The following examples describe the preparation of compounds 2 through 21 as shown in scheme 1.

Example 1

Preparation of N-Methoxy-N'-methyl-4-nitrobenzenecarboxide (2)

To a mixture of p-nitrobenzoyl chloride (15 g, 0.08 mol), and N, O-dimethylhydroxylamine hydrochloride (8.5 g, 0.09 mol) in methylene chloride (250 mL) was added pyridine (14 g, 0.18 mol) dropwise in5 mi at 0° C. After stirring at such temperature for another 2 hours, the solvent was removed under reduced pressure. The residue was treated with ethyl acetate (100 ml) and 1N HCl (50 mL) and separated. The aqueous phase was extracted with ethyl acetate (50 mL). The combined organic phase was dried over $Na_2SO_4$. Removal of tie solvent gave product as yellow oil that crystallized upon treatment with ether-hexanes. The light yellow solid was collected by filtration to affords 12 g (yield: 71%) of the amide. M.p. 71–73° C.

Example 2

Preparation of N-Methoxy-N'-methyl-4-aminobenzenecarboxide (3)

The mixture of amide 2 (11 g, 52 mmol), 10% palladium on carbon (0.5 g), and methanol (250 ml) was agitated on a Parr shaker under 45 p.s.i. initial pressure. After 2 hours, no more hydrogen uptake was observed. The catalyst was filtered, washed with methanol, and the filtrate was evaporated in vacuum to afford a tan solid. The solid was chromatographed on a silica gel. Product was obtained as tan solid (9.5 g, 100%). M.p. 91–92° C. $^1$HNMR ($CDCl_3$): 7.65 (d, 2H), 6.66 (d, 2H), 3.95 (br, 2H), 3.60 (s, 3H), 3.34 (s, 3H).

Example 3

Preparation of N-Methoxy-N'-methyl-4-acetylaminobenzenecarboxide (4)

To the mixture of the amine 3 (1.8 g, 10 mmol) in chloroform (50 mL) was added acetic anhydride (4 mL) and catalytic amount of DMAP (20 mg) at 0° C. After stirring at such temperature for 1.5 hour, no more starting materials were detected from TLC. The reaction was quenched by adding ice water, extracted with DCM twice. The organic layer was washed with brine, dried over $Na_2SO_4$. Removal of the solvent afforded the crude product. White crystal product was obtained upon recrystallization from ethyl acetate and hexanes (2.15 g). $^1$HNMR ($CDCl_3$): 7.7 (d, J=8.7 Hz, 2H), 7.55 (d, J=8.7 Hz, 2H), 3.56 (s, 3H), 3.36 (s, 3H), 2.19 (s, 3H).

Example 4

Preparation of 4-Methylthio-2-(4-acetylaminobenzoyl)-benzaldehyde (6)

To a solution of N,N,N'-trimethylethylenediamine (TMEDA) (4.8 mL, 39 mmol) in THF (80 ml) was added n-BuLi (2.5 M, 16 mL) at −20° C. in 30 min, followed by adding 4-methylthiobenzenaldehyde (5, 5.22 mL, 39.2 mmol), and n-BuLi (2.5 M, 16 mL) in 30 min. After keeping the reaction mixture in freezer overnight, amide 4 was added at −78° C. The reaction mixture was allowed to warm up to room temperature, and continued to stir for another 4 hours. The reaction was quenched by adding ice water, followed by extraction with ethyl acetate three times. The organic phase was washed with brine, dried over $Na_2SO_4$. Removal of the solvent afforded the crude product, which was purified by chromatograph on a silica gel, gave the desired product (3.89 g, 67%). $^1$HNMR ($CDCl_3$): 9.83 (s, 1H), 8.11 (br, 1H), 7.96 (d, J=8.7 Hz, 1H), 7.70 (d, J=8.8 Hz, 2H), 7.54 (d, J=8.8 Hz, 2H), 7.13 (m, 1H), 6.93 (d, J=2.7 Hz, 1H), 2.52 (s, 3H), 2.24 (s, 3H).

Example 5

Preparation of 1-(4-Acetylaminophenyl)-7-methylthiophtalazine (7)

To a solution of the benzophenone 6 (3.4 g, 10.85 mmol) in ethyl alcohol (100 mL) was added hydrazine (3.0 mL, 3 eq). The resulting solution was refluxed for 3 hour. The solvent was removed under reduced pressure. Recrystallization of the crude product in DCM and hexanes gave the product (2.3 g, 61%). $^1$HNMR ($CDCl_3$): 9.43 (s, 1H), 8.85 (br, 1H), 7.94 (d, J=8.6 Hz, 1H), 7.75 (m, 4H), 7.58 (d, J=8.6 Hz, 2H), 2.52 (s, 3H), 2.23 (s, 3H).

Example 6

Preparation of 4-(4-Acetylaminophenyl)-1,2-dihydro-1-methyl-6-methylthiophthalazine (8)

To a solution of the phthalazine 7 (1.2 g, 3.88 mmol) in THF (150 mL) was added methyl lithium (1.4 M, 11 mL) at 0° C. The resulting dark brown solution was stirred 2 hours. Ice water was added to quench the reaction. The aqueous phase was extracted with DCM three times. The combined organic phase was dried over $Na_2SO_4$. Removal of the solvent afforded the crude product, which was used directly for the next step.

Example 7

Preparation of 4-(4-Acetylaminophenyl)-1,2-dihydro-1-methyl-2-ethylcarbamoyl-6-methylthiophthalazine (9)

To a solution of dihydrophthalazine 8 in chloroform was added ethyl isocyanate (3 eq) at room temperature. The resulting solution was stirred at such temperature for a few days until there is no starting material left from TLC. The solvent was removed under reduced pressure. Purification of the crude product by using a silica gel gave the desired products 9 (Yield: 50%). $^1$HNMR ($CDCl_3$): 7.70–7.55 (m, 5H), 7.35 (dd, J=4.3 Hz, 1H), 7.19 (m, 2H), 6.53 (br, 1H), 5.73 (q, J=13.2 Hz, 1H), 3.42 (m, 2H), 2.40 (s, 3H), 2.25 (s, 3H), 1.22 (m, 6H).

Example 8

Preparation of 4-(4-Acetylaminophenyl)-1,2-dihydro-1-methyl-2-propylcarbamoyl-6-methylthiophthalazine (10)

In a similar way to the preparation of 9, 10 was obtained by reacting 8 with n-propyl isocyanate (Yield: 72%).

¹HNMR (CDCl₃): 7.68 (br, 1H), 7.65 (d, J=8.9 Hz, 2H), 7.50 (d, J=8.9 Hz, 2H), 7.38–7.25 (m, 2H), 7.09 (d, J=2.8 Hz, 1H), 6.85 (br, 1H), 5.72 (q, J=13.2 Hz, 1H), 3.32 (m, 2H), 2.40 (s, 3H), 2.24 (s, 3H), 1.60 (m, 2H), 1.25 (d, J=6.6 Hz, 3H), 0.95 (t, J=7.3 Hz, 3H).

Example 9

Preparation of 4-(4-Acetylaminophenyl)-1,2-dihydro-1-methyl-2-butylcarbamoyl-6-methylthiophthalazine (11)

In a similar way to the preparation of 9, 11 was obtained by treating 8 with n-butyl isocyanate (Yield: 88%). ¹HNMR (CDCl₃): 7.95 (br, 1H), 7.72–7.53 (m, 4H), 7.35 (dd, J=4.3 Hz, 1H), 7.19 (m, 2H), 6.53 (br, 1H), 5.72 (q, J=13.2 Hz, 1H), 3.42 (m, 2H), 2.40 (s, 3H), 2.21 (s, 3H), 1.52–1.20 (m, 7H), 0.93 (t, J=7.3 Hz, 3H).

Example 10

Preparation of 4-(4-Aminophenyl)-1,2-dihydro-1-methyl-2-ethylcarbamoyl-6-methylthiophthalazine (12)

The solution of acetyl amide 9 in methanol and NaOH (2 N) was refluxing until there is no more starting material left monitored by TLC. The solution was diluted with water, and extracted with DCM three times. Removal of the solvent afforded the crude product, which was purified by using a silica gel column, gave the desired products 12 (Yield: 87%). 1HNMR (CDCl₃): 7.45 (d, J=8.6 Hz, 2H), 7.35–7.25 (m, 4H), 6.78 (d, J=8.6 Hz, 2H), 6.53 (br, 1H), 5.60 (q, J=13.2 Hz, 1H), 3.42 (m, 2H), 2.40 (s, 3H), 1.22 (m, 6H).

Example 11

Preparation of 4-(4-Aminophenyl)-1,2-dihydro-1-methyl-2-propylcarbamoyl-6-methylthiophthalazine (13)

In a similar way to the preparation of 12, 13 was obtained from 10 (Yield: 78%). ¹HNMR (CDCl₃): 7.43 (d, J=8.6 Hz, 2H), 7.35–7.145 (m, 4H), 6.87 (d, J=8.6 Hz, 2H), 6.60 (br, 1H), 5.72 (q, J=1 3.2 Hz, 1H), 3.42 (m, 2H), 2.40 (s, 3H), 1.60 (m, 2H), 1.25 (d, J=6.6 Hz, 3H), 0.95 (t, J=7.3 Hz, 3H).

Example 12

Preparation of 4-(4-Aminophenyl)-1,2-dihydro-1-methyl-2-butylcarbamoyl-6-methylthiophthalazine (14)

In a similar way to the preparation of 12, 14 was obtained from 11 (Yield: 82%). ¹HNMR (CDCl₃): 7.48 (d, J=8.6 Hz, 2H), 7.35–7.25 (m, 4H), 6.89 (d, J=8.6 Hz, 2H), 6.53 (br, 1H), 5.72 (q, J=13.2 Hz, 1H), 3.42 (m, 2H), 2.40 (s, 3H), 2.23 (s, 3H), 1.40 (m, 4H), 1.25 (d, J=6.6 Hz, 3H), 0.93 (t, J=7.3 Hz, 3H).

Example 13

Preparation of 4-(4-Acetylaminophenyl)-1,2-dihydro-6-methylthiophthalazine (15)

To a solution of the phthalazine 7 (130 mg, 0.42 mmol) in acetic acid (7 mL) was added NaBH₃CN in portions. After stirring for 15 min, water was added. The aqueous phase was neutralized by NaHCO₃, and then extracted with DCM. The combined organic phase was dried over Na₂SO₄. Removal of the solvent afforded the product (97 mg, 74%) which can be used directly for next step.

Example 14

Preparation of 4-(4-Acetylaminophenyl)-1,2-dihydro-2-ethylcarbamoyl-6-methylthiophthalazine (16)

In a similar way to the preparation of 9, 16 was obtained by reacting 15 with ethyl isocyanate (Yield: 55%). ¹HNMR (CDCl₃): 7.70–7.55 (m, 5H), 7.32 (dd, J=4.3 Hz, 1H), 7.19 (m, 2H), 6.57 (br, 1H), 4.85 (s, 2H), 3.45 (m, 2H), 2.40 (s, 3H), 2.21 (s, 3H), 1.22 (m, 3H).

Example 15

Preparation of 4-(4-Acetylaminophenyl)-1,2-dihydro-2-propylcarbamoyl-6-methylthiophthalazine (17)

In a similar way to the preparation of 9, 17 was obtained by reacting 16 with n-propyl isocyanate (Yield: 64%). ¹HNMR (CDCl₃): 7.56 (d, J=8.9 Hz, 2H), 7.39 (dd, J=4.3 Hz, 1H), 7.15 (m, 2H), 7.02 (d, J=8.9 Hz, 2H), 4.80 (s, 2H), 3.32 (m, 2H), 2.38 (s, 3H), 2.23 (s, 3H), 1.50 (m, 2H), 0.95 (t, J=7.3 Hz, 3H).

Example 16

Preparation of 4-(4-Acetylaminophenyl)-1,2-dihydro-2-butylcarbamoyl-6-methylthiophthalazine (18)

In a similar way to the preparation of 9, 18 was obtained by treating 15 with n-butyl isocyanate (Yield: 79%). ¹HNMR (CDCl₃): 8.02 (br, 1H), 7.81–7.52 (m, 4H), 7.32 (dd, J=4.3 Hz, 1H), 7.16 (m, 2H), 6.74 (br, 1H), 4.80 (s, 2H), 3.42 (m, 2H), 2.40 (s, 3H), 2.21 (s, 3H), 1.52–1.20 (m, 4H), 0.93 (t, J=7.3 Hz, 3H).

Example 17

Preparation of 4-(4-Aminophenyl)-1,2-dihydro-2-ethylcarbamoyl-6-methylthiophthalazine (19)

In a similar way to the preparation of 12, 19 was obtained from 16 (Yield: 77%). ¹HNMR (CDCl₃): 7.48 (d, J=8.6 Hz, 2H), 7.35–7.25 (m, 4H), 6.73 (d, J=8.6 Hz, 2H), 6.53 (br, 1H), 4.83 (s, 2H), 3.42 (m, 2H), 2.40 (s, 3H), 1.22 (m, 3H).

Example 18

Preparation of 4-(4-Aminophenyl)-1,2-dihydro-2-propylcarbamoyl-6-methylthiophthalazine (20)

In a similar way to the preparation of 12, 20 was obtained from 19 (Yield: 81%). ¹HNMR (CDCl₃): 7.56 (br, 1H), 7.53 (d, J=8.9 Hz, 2H), 7.35 (dd, J=4.3 Hz, 1H), 7.19 (m, 2H), 6.95 (d, J=8.9 Hz, 2H), 4.83 (s, 2H), 3.32 (m, 2H), 2.40 (s, 3H), 1.52 (m, 2H), 0.93 (t, J=7.3 Hz, 3H).

Example 19

Preparation of 4-(4-Aminophenyl)-1,2-dihydro-2-butylcarbamoyl-6-methylthiophthalazine (21)

In a similar way to the preparation of 12, 21 was obtained from 18 (Yield: 64%). ¹HNMR (CDCl₃): 7.46 (d, J=8.6 Hz, 2H), 7.35–7.25 (m, 4H), 6.87 (d, J=8.6 Hz, 2H), 6.77 (br, 1H), 4.80 (s, 2H), 3.42 (m, 2H), 2.40 (s, 3H), 1.40 (m, 4H), 0.93 (t, J=7.3 Hz, 3H).

Example 20

Inhibition of Ca²⁺ Flux in a Primary Cortical Cell Cultures

Examples of the disclosed compounds were analyzed for inhibition of $Ca^{2+}$ flux in a primary cortical cell cultures. The inhibition analysis of $Ca^{2+}$ flux in a primary cortical cell cultures was made with a fluid-handling robot and $Ca^{2+}$-fluorimetry based assays were used to measure activity of the AMPA receptor The principle is that an intracellular $Ca^{2+}$ flux occurs whenever a channel or receptor is activated at the membrane. That increase can come from an extracellular or intracellular source. Inhibition of a receptor would be represented as a decrease in the level of intracellular calcium and can be lower than the saline level. Fluo 3AM was used as the calcium fluoroprobe because it gives one of the highest signals per molecule of dye.

Method: Approximately 25,000 cells isolated from neonatal rat cortex were cultured per well of a 96-well tissue culture plate (Becton Dickinson, PDL BioCoat plate). Cells were loaded with the AM ester of Fluo 3AM, a calcium dye (final concentration of 2 $\mu$M) for 40 min at 37° C. All solutions including dye, saline, Kainate+APV and SYM compounds were added to the culture plates with the robot to ensure uniformity. A dose response to SYM compounds in the presence of 100 $\mu$M kainate+50 $\mu$M APV was observed. SYM compounds were tested at the following doses: 0.01, 0.1, 0.5, 1.0, 5.0, 10.0, 15.0, 20.0, 25.0, 30.0 $\mu$M. Eight replicate wells were assayed at each dose. Internal controls were saline treatment and kainate plus APV alone. The results are expressed as a percent change in fluorescence=(Fluorescence reading 2-Fluorescence reading 1)/F1*100.

It is understood that the disclosed invention is not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a ", "an", and "the" include plural reference unless the context clearly dictates otherwise. Thus, for example, reference to "a host cell" includes a plurality of such host cells, reference to "the antibody" is a reference to one or more antibodies and equivalents thereof known to those skilled in the art, and so forth.

Unless defined otherwise, all technical and scientific terms used herein have the same meanings as commonly understood by one of skill in the art to which the disclosed invention belongs. Although ally methods and materials similar or equivalent to those described herein can be used in the practice or testing of the present invention, the preferred methods, devices, and materials are as described. Publications cited herein and the material for which they are cited are specifically incorporated by reference. Nothing herein is to be construed as an admission that the invention is not entitled to antedate such disclosure by virtue of prior invention.

Those skilled in the art will recognize, or be able to ascertain using no more than routine experimentation, many equivalents to the specific embodiments of the invention described herein. Such equivalents are intended to be encompassed by the following claims.

We claim:

1. A method for treating a patient having a disorder associated with excessive activation of the α-amino-3-hydroxy-5-methyl-4-isooxazoleproprionic acid (AMPA) subtype of the ionotropic excitatory amino acid (EAA) receptors, the method comprising administering to the patient, in an effective amount to alleviate the symptoms of the disorder, a compound of Formula I:

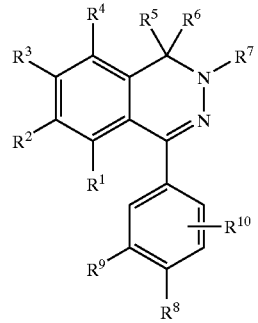

wherein
$R^1$, $R^2$, $R^3$ and $R^4$ are independently
H,
HO,
$R^{11}O-$,
halogen
C1–C3-alkyl,
$CF_3$,
$R^{12}CO_2-$,
$R^{12}O_2C-$,
$R^{12}CO-$,
$R^{12}CONH-$,
$R^{12}NHCO-$,
$R^{12}NHCO_2-$,
$R^{12}OCONH-$,
$R^{12}O_2S-$,
$R^{12}OS-$, or
$R^{13}R^{14}N-$; or
$R^1$ and $R^2$, or $R^2$ and $R^3$, or $R^3$ and $R^4$ taken together can be
$-SCH_2S-$,
$-SCH_2O-$,
$-OCH_2S-$,
$-SCH_2CH_2S-$,
$-SCH_2CH_2O-$, or
$-OCH_2CH_2S-$;
wherein at least one of $R^1$, $R^2$, $R^3$ and $R^4$ must be a C1–C3-alkylthio group,
$R^5$ and $R^6$ are independently
H,
C1–C6-alkyl,
C3–C6-alkenyl,
C3–C6-cycloalkyl, or
phenyl or substituted phenyl, wherein the phenyl is substituted with one or two substituents selected from the group consisting of C1–C3-alkyl, halogen, $R^{11}O-$, $CF_3$, $R^{12}O_2S-$, $R^{12}OS-$, $R^{12}CO$, $R^{12}CO_2-$, $R^{12}O_2C-$, $R^{12}CONH-$, $R^{12}NHCO-$, $R^{12}NHCO_2-$, $R^{12}OCONH-$, and $R^{13}R^{14}N-$; or
$R^5$ and $R^6$ taken together can be C3–C6-cycloalkyl;
$R^7$ is
$R^{13}R^{14}NCO-$,
$R^{13}R^{14}NCS-$,
$R^{13}R^{14}N(HCR^{15})-$,
$R^{15}OCO-$,
$R^{13}CO-$,
$R^{13}R^{14}NCH_2CO-$, $R^{12}O_2C-(CH_2)_n-$,
$R^{13}R^{14}NCO-(CH_2)_n-$,
$NC-(CH_2)_n-$,
H,
C1–C6-alkyl,
C3–C6-alkenyl, or
C3–C6-cycloalkyl; or $R^6$ and $R^7$ taken together can be
$-(CH_2)_mCH_2(R^{13})NCO-$,
$-(CH_2)_mCH_2OCO-$, or
$-(CH_2)_mCH_2CH_2CO-$;

$R^8$ and $R^9$ are independently
H,
$R^{13}R^{14}N-$,
$R^{13}R^{14}N(HCR^{15})-$,
$R^{12}HNCO-$, or
$R^{12}CONH-$;

$R^{10}$ is
H,
halogen,
HO,
$R^{11}O-$,
$R^{13}R^{14}N-$,
C1–C3-alkyl,
$CF_3$,
$R^{12}CO_2-$,
$R^{12}CO-$, or
$R^{12}CONH-$;

$R^{11}$ is C1–C3-alkyl;

$R^{12}$ is H or C1–C3-alkyl;

$R^{13}$ and $R^{14}$ are independently
H,
C1–C10-alkyl,
C1–C6-perfluoroalkyl,
C3–C10-alkenyl, or
C3–C6-cycloalkyl; or $R^{13}$ and $R^{14}$ taken together can be C3–C6-cycloalkyl;

$R^{15}$ is C1–C6-alkyl, C3–C6-alkenyl, or C3–C6-cycloalkyl;

n is 1 to 6;

m is 0 to 2;

and pharmaceutically acceptable salts thereof;
wherein $R^8$ and $R^9$ cannot be both be H,
in combination with a pharmaceutically acceptable carrier.

2. The method of claim 1 wherein, in the compound of Formula I, one of four substituents of $R^1$, $R^2$, $R^3$ and $R^4$ must be C1–C3-alkylthio group, the other substituents are independently H, $R^{11}O-$, $R^{11}S-$, halogen, or C1–C3-alkyl;

$R^2$ and $R^3$ taken together can be $-SCH_2S-$, $SCH_2O-$, or $-OCH_2S-$;

$R^7$ is
$R^{13}R^{14}NCO-$,
$R^{13}R^{14}NCS-$,
$R^{13}R^{14}N(HCR^{15})-$,
$R^{15}OCO-$,
$R^{13}CO-$, or
H;

$R^8$ and $R^9$ are independently H, $H_2N-$ or $CH_3CONH-$;
or pharmaceutically acceptable salts thereof.

3. The method of claim 2 wherein the compound of Formula I is selected from the group consisting of
4-(4-Aminophenyl)-1,2-dihydro-1-methyl-2-ethylcarbamoyl-6-methylthiophthalazine, 4-(4-Aminophenyl)-1,2-dihydro-1-methyl-2-n-propylcarbamoyl-6-methylthiophthalazine, 4-(4-Aminophenyl)-1,2-dihydro-1-methyl-2-n-butylcarbamoyl-6-methylthiophthalazine, 4-(4-Aminophenyl)-1,2-dihydro-2-ethylcarbamoyl-6-methylthiophthalazine, 4-(4-Aminophenyl)-1,2-dihydro-2-n-propylcarbamoyl-6-methylthiophthalazine, and 4-(4-Aminophenyl)-1,2-dihydro-2-n-butylcarbamoyl-6-methylthiophthalazine.

4. The method of claim 1 wherein the disorder is selected from the group consisting of neurological, neuropsychological, neuropsychiatric, neurodegenerative, neuropsychopharmacological and functional disorders.

5. The method of claim 2 wherein the disorder is selected from the group consisting of neurological, neuropsychological, neuropsychiatric, neurodegenerative, neuropsychopharmacological and functional disorders.

6. The method of claim 3 wherein the disorder is selected from the group consisting of neurological, neuropsychological, neuropsychiatric, neurodegenerative, neuropsychopharmacological and functional disorders.

7. A method for treating a patient having a disorder associated with excessive activation of the α-amino-3-hydroxy-5-methyl-4-isooxazoleproprionic acid (AMPA) subtype of the ionotropic excitatory amino acid (EAA) receptors, the method comprising administering to the patient, in an effective amount to alleviate the symptoms of the disorder, a compound of Formula II:

wherein
$R^1$, $R^2$, $R^3$ and $R^4$ are independently
H,
HO,
$R^{11}O-$,
halogen,
C1–C3-alkyl,
$CF_3$,
$C^{12}CO_2-$,
$R^{12}O_2C-$,
$R^{12}CO-$,
$R^{12}CONH-$,
$R^{12}NHCO-$,
$R^{12}NHCO_2-$,
$R^{12}OCONH-$,
$R^{12}O_2S-$,
$R^{12}OS-$, or
$R^{13}R^{14}N-$; or $R^1$ and $R^2$, or $R^2$ and $R^3$, or $R^3$ and $R^4$ taken together can be
$-SCH_2S-$,
$-SCH_2O-$,
$-OCH_2S-$,
$-SCH_2CH_2S-$,
$-SCH_2CH_2O-$, or —OCH$_2$CH$_2$S—;
wherein at least one of R$^1$, R$^2$, R$^3$ and R$^4$ must be a C1–C3-alkylthio group;
R$^5$ is
H,
C1–C6-alkyl,
C3–C6-alkenyl,
C3–C6-cycloalkyl,
phenyl or substituted phenyl, wherein the phenyl is substituted with one or two substituents selected from the group consisting of C1–C3-alkyl, halogen, R$^{11}$O—, CF$_3$—, R$^{12}$O$_2$S—, R$^{12}$OS—, R$^{12}$CO, R$^{12}$CO$_2$—, R$^{12}$O$_2$C—, R$^{12}$CONH—, R$^{12}$NHCO—, R$^{12}$NHCO$_2$—, R$^{12}$OCONH—, or R$^{13}$R$^{14}$N—;
R$^{11}$ is C1–C3-alkyl;
R$^{12}$ is H or C1–C3-alkyl;
R$^{13}$ and R$^{14}$ are independently
H,
C1–C10-alkyl,
C1–C6-perfluoroalkyl,
C3–C10-alkenyl, or
C3–C6-cycloalkyl; or
R$^{13}$ and R$^{14}$ taken together can be C3–C6-cycloalkyl;
R$^{15}$ is C1–C6-alkyl, C3–C6-alkenyl, or C3–C6-cycloalkyl;
R$^{16}$ and R$^{17}$ are independently
H,
halogen,
C1–C3-alkyl,
R$^{12}$O—,
CF$_3$—, or
R$^{12}$CO$_2$—;
R$^{18}$ and R$^{19}$ are independently
H,
R$^{13}$R$^{14}$N—,
R$^{13}$HNC(NH)—, or
R$^{12}$CONH—,
or pharmaceutically acceptable salts thereof;
wherein R$^{18}$ and R$^{19}$ cannot both be H,
in combination with a pharmaceutically acceptable carrier.

8. The method of claim 7 wherein, in the compound of Formula II, one of four substituents of R$^1$, R$^2$, R$^3$ and R$^4$ must be a C1–C3-alkylthio group, the other substituents are independently H, R$^{11}$O—, R$^{11}$S—, halogen or C1–C3-alkyl;
R$^2$ and R$^3$ taken together can be —SCH$_2$S—, —SCH$_2$O—, or —OCH$_2$S—;
R$^{18}$ and R$^{19}$ are independently H, H$_2$N—, or CH$_3$CONH—; or pharmaceutically acceptable salts thereof.

9. The method of claim 8 wherein the compound of Formula II is selected from the group consisting of
1-(4-Aminophenyl)-6-methylthiophthalazine, 1-(4-Acetylaminophenyl)-6-methylthiophthalazine, 1-(4-Aminophenyl)-7-methylthiophthalazine, 1-(4-Aminophenyl)-4-methyl-6-methylthiophthalazine, 1-(4-Acetylaminophenyl)-4-methyl-6-methylthiophthalazine, 1-(4-Aminophenyl)-4-methyl-7-methylthiophthalazine, 1-(4-Acetylaminophenyl)-4-methyl-7-methylthiophthalazine.

10. The method of claim 7 wherein the disorder is selected from the group consisting of neurological, neuropsychological, neuropsychiatric, neurodegenerative, neuropsychopharmacological and functional disorders.

11. The method of claim 8 wherein the disorder is selected from the group consisting of neurological, neuropsychological, neuropsychiatric, neurodegenerative, neuropsychopharmacological and functional disorders.

12. The method of claim 9 wherein the disorder is selected from the group consisting of neurological, neuropsychological, neuropsychiatric, neurodegenerative, neuropsychopharmacological and functional disorders.

13. A method for decreasing the excessive flux of ions through an α-amino-3-hydroxy-5methyl-4-isooxazoleproprionic acid (AMPA) subtype of the ionotropic excitatory amino acid (BAA) receptors, the method comprising contacting a cortical cell with an effective amount of a compound of Formula I:

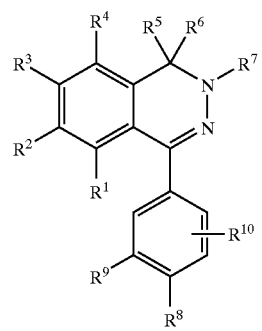

wherein
R$^1$, R$^2$, R$^3$ and R$^4$ are independently
H,
HO,
R$^{11}$O—,
halogen,
C1–C3-alkyl,
CF$_3$,
R$^{12}$CO$_2$—,
R$^{12}$O$_2$C—,
R$^{12}$CO—,
R$^{12}$CONH—,
R$^{12}$NHCO—,
R$^{12}$NHCO$_2$—,
R$^{12}$OCONH—,
R$^{12}$O$_2$S—,
R$^{12}$OS—, or
R$^{13}$R$^{14}$N—; or
R$^1$ and R$^2$, or R$^2$ and R$^3$, or R$^3$ and R$^4$ taken together can be
—SCH$_2$S—,
—SCH$_2$O—,
—OCH$_2$S—,
—SCH$_2$CH$_2$S—,
—SCH$_2$CH$_2$O—, or
—OCH$_2$CH$_2$S—;
wherein at least one of R$^1$, R$^2$, R$^3$ or R$^4$ must be a C1–C3-alkylthio group,
R$^5$ and R$^6$ are independently
H,
C1–C6-alkyl,
C3–C6-alkenyl,
C1–C6-cycloalkyl, or
phenyl or substituted phenyl, wherein the phenyl is substituted with one or two substituents selected from the group consisting of C1–C3-alkyl, halogen, R$^{11}$O—, CF$_3$, R$^{12}$O$_2$S—, R$^{12}$OS—, R$^{12}$CO, R$^{12}$CO$_2$—, R$^{12}$O$_2$C—, R$^{12}$CONH—, R$^{12}$NHCO—, R$^{12}$NHCO$_2$—, R$^{12}$OCONH—, and R$^{13}$R$^{14}$N—; or $R^5$ and $R^6$ taken together can be C3–C6-cycloalkyl,
$R^7$ is
    $R^{13}R^{14}NCO—$,
    $R^{13}R^{14}NCS—$,
    $R^{13}R^{14}N(HCR^{15})—$,
    $R^{15}OCO—$,
    $R^{13}CO—$,
    $R^{13}R^{14}NCH_2CO—$,
    $R^{12}O_2C—(CH_2)_n—$,
    $R^{13}R^{14}NCO—(CH_2)_n—$,
    $NC—(CH^2)_n—$,
    H,
    C1–C6-alkyl,
    C3–C6-alkenyl, or
    C3–C6-cycloalkyl; or
$R^6$ and $R^7$ taken together can be
    $—(CH_2)_mCH_2(R^{13})NCO—$,
    $—(CH_2)_mCH_2OCO—$, or
    $—(CH_2)_mCH_2CH_2CO—$;
$R^8$ and $R^9$ are independently
    H,
    $R^{13}R^{14}N—$,
    $R^{13}R^{14}N(HCR^{15})—$,
    $R^{12}HNCO—$, or
    $R^{12}CONH—$;
$R^{10}$ is
    H,
    halogen,
    HO,
    $R^{11}O—$,
    $R^{13}R^{14}N—$,
    C1–C3-alkyl,
    $CF_3$,
    $R^{12}CO_2—$,
    $R^{12}CO—$, or
    $R^{12}CONH—$;
$R^{11}$ is C1–C3-alkyl;
$R^{12}$ is H or C1–C3-alkyl;
$R^{13}$ and $R^{14}$ are independently
    H,
    C1–C10-alkyl,
    C1–C6-perfluoroalkyl,
    C3–C10-alkenyl, or
    C3–C6-cycloalkyl; or
$R^{13}$ and $R^{14}$ taken together can be C3–C6-cycloalkyl;
$R^{15}$ is C1–C6-alkyl, C3–C6-alkenyl, or C3–C6-cycloalkyl;
n is 1 to 6;
m is 0 to 2;
or pharmaceutically acceptable salts thereof;
    wherein $R^8$ and $R^9$ cannot both be H,
in combination with a pharmaceutically acceptable carrier
    so that the excessive flux of ions through the AMPA receptor is decreased.

14. The method of claim 13 wherein, in the compound of Formula I, one of four substituents of $R^1$, $R^2$, $R^3$ and $R^4$ must be C1–C3-alkylthio group, the other substituents are independently H, $R^{11}O—$, $R^{11}S—$, halogen or C1–C3-alkyl;
    $R^2$ and $R^3$ taken together can be $—SCH_2S—$, $SCH_2O—$, or $—OCH_2S—$;
    $R^7$ is
        $R^{13}R^{14}NCO—$,
        $R^{13}R^{14}NCS—$,
        $R^{13}R^{14}N(HCR^{15})—$,
        $R^{15}OCO—$,
        $R^{13}CO—$, or
        H;
    $R^8$ and $R^9$ are independently H, $H_2N—$ or $CH_3CONH—$;
or pharmaceutically acceptable salts thereof.

15. The method of claim 14 wherein the compound of Formula I is selected from the group consisting of
    4-(4-Aminophenyl)-1,2-dihydro-1-methyl-2-ethylcarbamoyl-6-methylthiophthalazine, 4-(4-Aminophenyl)-1,2-dihydro-1-methyl-2-n-propylcarbamoyl-6-methylthiophthalazine, 4-(4-Aminophenyl)-1,2-dihydro-1-methyl-2-n-butylcarbamoyl-6-methylthiophthalazine, 4-(4-Aminophenyl)-1,2-dihydro-2-ethylcarbamoyl-6-methylthiophthalazine, 4-(4-Aminophenyl)-1,2-dihydro-2-n-propylcarbamoyl-6-methylthiophthalazine, and 4-(4-Aminophenyl)-1,2-dihydro-2-n-butylcarbamoyl-6-methylthiophthalazine.

16. A method for decreasing the excessive flux of ions through an α-amino-3-hydroxy-5-methyl-4-isooxazoleproprionic acid (AMPA) subtype of the ionotropic excitatory amino acid (EAA) receptors, the method comprising contacting a cortical cell with an effective amount of a compound of Formula II:

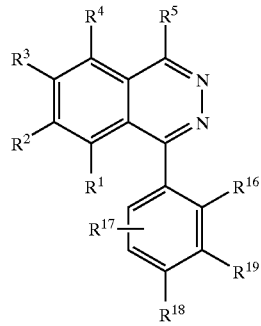

wherein
    $R^1$, $R^2$, $R^3$ and $R^4$ are independently
        H,
        HO,
        $R^{11}O—$,
        halogen,
        C1–C3-alkyl,
        $CF_3$,
        $R^{12}CO_2—$,
        $R^{12}O_2C—$,
        $R^{12}CO—$,
        $R^{12}CONH—$,
        $R^{12}NHCO—$,
        $R^{12}NHCO_2—$,
        $R^{12}OCONH—$,
        $R^{12}O_2S—$,
        $R^{12}OS—$, or
        $R^{13}R^{14}N—$; or
    $R^1$ and $R^2$, or $R^2$ and $R^3$, or $R^3$ and $R^4$ taken together can be
        $—SCH_2S—$,
        $—SCH_2O—$,
        $—OCH_2S—$,
        $—SCH_2CH_2S—$,
        $—SCH_2CH_2O—$, or
        $—OCH_2CH_2S—$;

wherein at least one of $R^1$, $R^2$, $R^3$ or $R^4$ must be a C1–C3-alkylthio group;

$R^5$ is
   H,
   1–C6-alkyl,
   C3–C6-alkenyl,
   C3–C6-cycloalkyl,
   phenyl or substituted phenyl, wherein the phenyl is substituted with one or two substituents selected from the group consisting of C1–C3-alkyl, halogen, $R^{11}O$—, $CF_3$—, $R^{12}O_2S$—, $R^{12}OS$—, $R^{12}CO$, $R^{12}CO_2$—, $R^{12}O_2C$—, $R^{12}CONH$—, $R^{12}NHCO$—, $R^{12}NHCO_2$—, $R^{12}OCONH$—, or $R^{13}R^{14}N$—;

$R^{11}$ is C1–C3-alkyl;

$R^{12}$ is H or C1–C3-alkyl;

$R^{13}$ and $R^{14}$ are independently
   H,
   C1–C10-alkyl,
   C1–C6-perfluoroalkyl,
   C3–C10-alkenyl, or
   C3–C6-cycloalkyl; or $R^{13}$ and $R^{14}$ taken together can be C3–C6-cycloalkyl;

$R^{15}$ C1–C6-alkyl, C3–C6-alkenyl, or C3–C6-cycloalkyl;

$R^{16}$ and $R^{17}$ are independently
   H,
   halogen,
   C1–C3-alkyl,
   $R^{12}O$—,
   $CF_3$—, or
   $R^{12}CO_2$—;

$R^{18}$ and $R^{19}$ are independently
   H,
   $R^{13}R^{14}N$—,
   $R^{13}HNC(NH)$—, or
   $R^{12}CONH$—;

or pharmaceutically acceptable salts thereof;
   wherein $R^{18}$ and $R^{19}$ cannot both be H, in combination with a pharmaceutically acceptable carrier
   so that the excessive flux of ions through the AMPA receptor is decreased.

17. The method of claim 16 wherein, in the compound of Formula II, one of four substituents of $R^1$, $R^2$, $R^3$ and $R^4$ must be a C1–C3-alkylthio group, the other substituents are independently H, $R^{11}O$—, $R^{11}S$—, halogen, or C1–C3-alkyl;

$R^2$ and $R^3$ taken together can be —$SCH_2S$—, —$SCH_2O$—, or —$OCH_2S$—;

$R^{18}$ and $R^{19}$ are independently H, $H_2N$—, or $CH_3CONH$—; or pharmaceutically acceptable salts thereof.

18. The method of claim 17 wherein the compound of Formula II is selected from the group consisting of
   1-(4-Aminophenyl)-6-methylthiophthalazine, 1-(4-Acetylaminophenyl)-6-methylthiophthalazine, 1-(4-Aminophenyl)-7-methylthiophthalazine, 1-(4-Aminophenyl)-4-methyl-6-methylthiophthalazine, 1-(4-Acetylaminophenyl)-4-methyl-6-methylthiophthalazine, 1-(4-Aminophenyl)-4-methyl-7-methylthiophthalazine, 1-(4-Acetylaminophenyl)-4-methyl-7-methylthiophthalazine.

\* \* \* \* \*